(12) United States Patent
Hu et al.

(10) Patent No.: US 7,475,866 B2
(45) Date of Patent: Jan. 13, 2009

(54) PULLING DEVICE FOR CONTAINER INSPECTION SYSTEM

(75) Inventors: Bin Hu, Beijing (CN); Shangmin Sun, Beijing (CN); Guang Yang, Beijing (CN); Yucheng Wu, Beijing (CN); Zhongrong Yang, Beijing (CN); Nan Jiang, Beijing (CN); Wanquan Shen, Beijing (CN); Jianjun Su, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 637 days.

(21) Appl. No.: 11/284,989

(22) Filed: Nov. 22, 2005

(65) Prior Publication Data

US 2006/0113163 A1    Jun. 1, 2006

(51) Int. Cl.
*B66D 1/26* (2006.01)
(52) U.S. Cl. ...................... 254/278; 254/338
(58) Field of Classification Search ........... 254/278, 254/338
See application file for complete search history.

(56) References Cited

U.S. PATENT DOCUMENTS

| 983,957 | A | * | 2/1911 | Trantham | ............ 254/338 |
|---|---|---|---|---|---|
| 1,918,742 | A | * | 7/1933 | Elrod | ............ 210/525 |
| 3,707,922 | A | * | 1/1973 | Dillon | ............ 104/114 |
| 3,713,548 | A | * | 1/1973 | Hanke | ............ 414/138.3 |
| 4,054,520 | A | * | 10/1977 | McGivern | ............ 210/122 |
| 4,927,537 | A | * | 5/1990 | Meurer | ............ 210/527 |
| 4,986,915 | A | * | 1/1991 | Meurer | ............ 210/527 |
| 5,051,027 | A | * | 9/1991 | Horton | ............ 405/3 |
| 7,093,823 | B2 | * | 8/2006 | Sevalie' | ............ 254/337 |

* cited by examiner

*Primary Examiner*—Emmanuel M Marcelo
(74) *Attorney, Agent, or Firm*—Kinney & Lange, P.A.

(57) ABSTRACT

The present invention discloses a pulling device for a container inspection system including a pulling vehicle (1) arranged inside an inspection passage, a winch (5) and wire tension mechanisms (6,6'). Front and rear ends of the pulling vehicle are connected to a wire rope so as to drive the pulling vehicle to move back and forth inside the inspection passage. The wire rope connected to front and rear ends of the pulling vehicle is wound around a wire tension mechanism arranged at front and rear ends of the inspection passage and is turned around by a swerving pulley (2) which is positioned at the same horizontal plane as that of the wire rope, the pulling vehicle, and the wire tension mechanisms, then the wire rope passes through the vertical pulley block, and finally it is connected to a single winding drum (4) of the winch (5) and wound around the single winding drum (4) respectively. Compared with the prior arts, the present invention is advantageous in reduction in equipment investment and decrease in area occupied by the pulling device. Further, the inspection operation can be carried out more reliably and safely.

4 Claims, 1 Drawing Sheet

PULLING DEVICE FOR CONTAINER INSPECTION SYSTEM

CROSS-REFERENCE TO RELATED APPLICATION

This application claims the benefit of Chinese Patent Application No. 200410009891.3 filed on Nov. 26, 2004 in the State Intellectual Property Office of China, the disclosure of which is incorporated herein by reference.

BACKGROUND OF THE INVENTION

1. Field of the Invention

The present invention relates to an inspection system for inspecting a container by obtaining images through radiation, more particularly, to a pulling device for a container inspection system.

2. Description of the Related Art

In the prior arts, the pulling type container inspection system, such as the large scale container inspection system manufactured by Haiman Corporation, Germany and British Airspace Corporation, has been developed in the early years of the nineties of 20$^{th}$ century. The above conventional container inspection system is devised as follows. Stationary accelerator which produces high energy x-ray as radiation source and stationary array detectors which receive x-ray passing through the container are mounted in an inspection passage which is capable of shielding radiation beams. A vehicle carrying the container which is pulled by a special pulling device so as to pass by the inspection passage. When the container passes x-ray, x-ray will transmit through the container and incident on the detectors. As a result, the density distribution of the objects contained in the container is presented in accordance with the variation of the intensity of x-ray. Then, the intensity of x-ray is converted into a corresponding gray degree of an image so that a perspective view of the objects contained in the container can be obtained.

A conventional pulling device is constructed as follows. Specifically, tracks are mounted inside an inspection passage, and a movable pulling vehicle is placed on the tracks. The head of the vehicle carrying the container stops on the pulling vehicle. The pulling vehicle is pulled by a traction system and moved along the tracks so that the vehicle carrying the container is pulled by the pulling device. As such, the vehicle carrying the container passes by the inspection passage.

However, the conventional pulling device of the container inspection system is disadvantageous in the following aspects. Two winding drums, two motors and two inverters are used so as to control the forward and backward movement of the pulling device respectively. Accordingly, the investment of the equipments is increased and the area occupied by the system is enlarged. Further, a traction force is applied to the pulling vehicle by wire ropes which are wound around the two winding drums. With this operation mode, it is difficult to control so as to achieve constant tensile force. Especially at the stage that the pulling vehicle is started or stopped, it may occur that a wire rope on one side is excessively slackened. As a result, the pulling operation can not be carried out stably, thus impeding normal operation of the inspection system.

SUMMARY OF THE INVENTION

The present invention has been made to overcome one or more of the above mentioned disadvantages. Accordingly, it is an object of the present invention to provide a pulling device for container inspection system in which the winch is configured to have a single winding drum. Accordingly, the investment of equipment is reduced and the area occupied by the system is decreased. Meanwhile, the inspection system of the present invention can provide constant tensile force which is continuously adjustable so that the operation of pulling device can be performed more reliably and more safely.

Additional aspects and advantages of the invention will be set forth in the description as follows.

The forgoing and other aspects of the present invention are achieved by providing a pulling device for container inspection system, comprising: a pulling vehicle arranged inside an inspection passage, wherein front and rear ends of said pulling vehicle are respectively connected with a wire rope for driving the pulling vehicle to move back and forth inside the inspection passage; a winch provided with a single winding drum; wire tension mechanisms arranged at front and rear ends of said inspection passage, respectively; wherein said wire rope connected to said front and rear ends of the pulling vehicle is wound around said wire tension mechanisms respectively, and is turned around by a swerving pulley which is positioned at the same horizontal plane as that of said wire tension mechanisms, then the wire rope passes through a vertical pulley block, and finally connected to said single winding drum of said winch and wound around said single winding drum respectively.

Preferably, in the aforesaid pulling device for a container inspection system, said vertical pulley block is composed of an upper vertical pulley and a lower vertical pulley which are positioned at different levels and spaced apart from each other in a horizontal direction, a lower rim of said lower vertical pulley are arranged at the same horizontal plane as that of said swerving wheel, and said position of the upper vertical pulley corresponds to that of said single winding drum, and said wire rope connected with front and rear ends of said pulling vehicle passes through said lower vertical pulley from the lower side of the lower vertical pulley, then passes through said upper vertical pulley from the upper side of said upper vertical pulley, finally winds around said single winding drum from the lower side to the upper side of said single winding drum in order, respectively.

Preferably, in the aforesaid pulling device for a container inspection system, said wire tension mechanism is an active type tension mechanism which generates a tensile force by use of a spring or similar device.

With the above construction, in the pulling device for the container inspection system of the present invention, the wire rope for driving the pulling vehicle back and forth is wound around the same winding drum. The winding drum with the constant diameter makes the wire ropes at both sides are synchronically retracted and slackened. Further, with the active type tension mechanism which generates a tensile force by use of a spring, the wire ropes are constantly kept in a state under an effective tensile force. Accordingly, the phenomenon that the wire ropes are entangled due to slack of the wire ropes will not occur. Moreover, the active type tension mechanism can make up the elongation resulting from permanent deformation of the wire ropes due to usage of long term. Compared with the prior arts, the investment of equipments is reduced and the area occupied by the system is decreased in the present invention.

BRIEF DESCRIPTION OF THE DRAWINGS

The above and other objects and advantages of the invention will become apparent and readily appreciated from the following description of the preferred embodiments, taken in conjunction with the accompanying drawings, in which.

DETAILED DESCRIPTION OF THE PREFERRED EMBODIMENT

Figure 1:
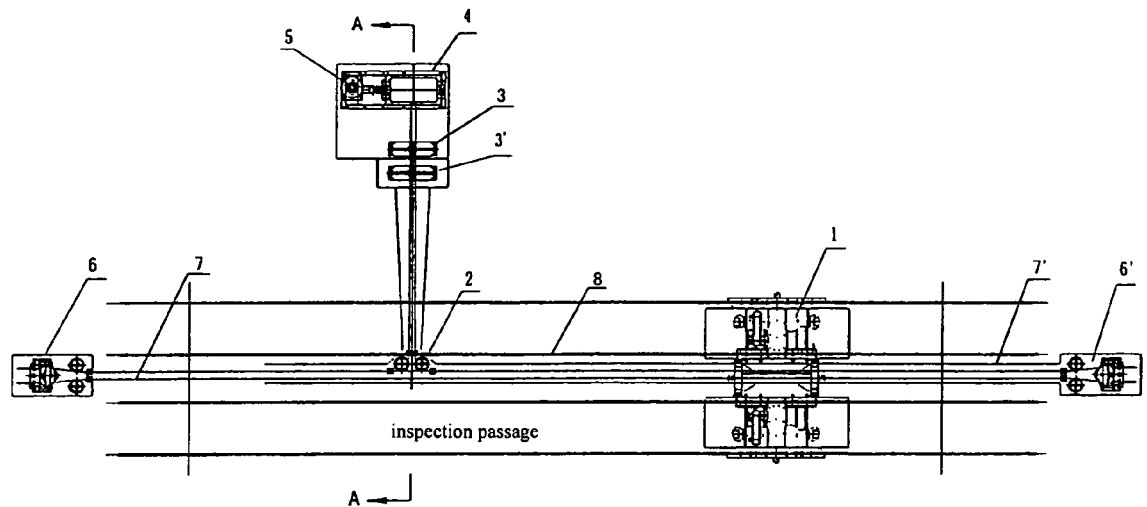
FIG. 1 is a schematic view of an arrangement of the pulling device of the container inspection system according to an embodiment of the present invention.

A preferred embodiment of the present invention will be described hereinafter in detail with reference to the attached drawings, wherein the like reference numerals refer to the like elements throughout the specification. The present invention may, however, be embodied in many different forms and should not be construed as being limited to the embodiment set forth herein; rather, this embodiment is provided so that the present disclosure will be thorough and complete, and will fully convey the concept of the invention to those skilled in the art.

Figure 2:
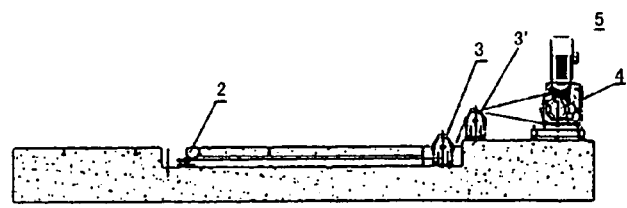
FIG. 2 is a sectional view taken along line A-A of FIG. 1.

Referring to FIGS. 1 and 2, the pulling device of the container inspection system of the present invention includes a pulling vehicle, a winch 5 disposed inside an inspection passage and wire rope tension mechanisms 6,6' disposed at front and rear ends inside the inspection passage. The wire rope tension mechanisms 6,6' are configured to be an active tensile construction which generates tensile force by use of a spring. The pulling vehicle 1 is placed on tracks 8 laid inside the inspection passage. The front and rear ends of the pulling vehicle 1 are connected with wires ropes, respectively, namely, a front end wire rope 7 and a rear end wire rope 7' for driving the pulling vehicle so that the pulling vehicle 1 can move back and forth inside the inspection passage. The front end wire rope 7 and a rear end wire rope 7' connected with the front and rear end of the pulling vehicle 1 are wound on the wire rope tension mechanisms 6,6' and conversed in direction by a swerving pulley 2 for conversing the direction of the wire ropes. The front end wire rope 7 and a rear end wire rope 7' pass through a swerving pulley 2 successively, a vertical pulley block, and then are connected with a single winding drum 4 of a winch 5 and wound thereon respectively.

The vertical pulley block is composed of an upper vertical pulley 3 and a lower vertical pulley 3' which are positioned at different levels and spaced apart from each other in a horizontal direction. Namely, the axis of the upper and lower vertical pulley 3,3' are positioned at different horizontal planes and parallel with the plane in which swerving pulley 2 is located, as shown in FIG. 2. The lower rim of the lower vertical pulley 3' are arranged at the same horizontal plane as that of the swerving wheel 2, and the position of the upper vertical pulley 3 corresponds to that of the single winding drum 4 of the winch 5. The front end wire rope 7 and a rear end wire rope 7' respectively pass through the lower vertical pulley 3' from the lower side of the lower vertical pulley 3', then passes through the upper side of the upper vertical pulley 3, finally winds around the single winding drum 4 from the lower side to the upper side of the single winding drum 4 respectively in the above order.

In operation, for instance, when the vehicle 1 is pulled to the direction along the left side of FIG. 1, the winch 5 applies a pulling force to the pulling vehicle 1 by the front end wire rope 7 wound around the single winding drum 4. Because this pulling force is greater than a tensile force which is applied to the front end wire rope 7 in the wire tension mechanism 6 around which the front end wire rope 7 (the wire tension mechanism 6 illustrated at the left side of FIG. 1) is wound, the upper and lower pulley block 3, 3' and the swerving pulley 2 are rotated. As a result, the wire rope 7' connected to the rear end of the pulling vehicle is discharged from the single winding drum 4. The discharged rear end wire rope 7' is tightened due to the tensile force by the wire tension mechanism 6' around which the rear end wire rope 7' (the wire tension mechanism illustrated at the right side of FIG. 1) is wound. In this case, a spring of the wire tension mechanism 6' tightens the released wire rope. When the spring of the wire tension mechanism 6 is not compressed, the pulling force applied to the front end wire rope 7 is transmitted to the pulling vehicle 1 so that the pulling vehicle 1 is driven to move. When the pulling vehicle is moved in a direction opposite to the above direction, the winch is rotated in an opposite direction. The other operations are similar to those as described above, and detailed descriptions for the operations are omitted here for purpose of brevity. In other words, the back and forth movement of the pulling vehicle 1 in the inspection passage is achieved by the forward and reverse rotation of the winding drum 5.

Although a preferred embodiment has been shown and described, it should be noted that the above embodiment is considered to be illustrative rather than limitative. The protection scope of the present invention is defined in the appended claims and their equivalents thereof. It would be appreciated by those skilled in the art that modifications, changes and replacement may be made in these embodiments without departing from the principles and spirit of the invention.

What is claimed is:

1. A pulling device for a container inspection system, comprising:

a pulling vehicle arranged inside an inspection passage, wherein front and rear ends of said pulling vehicle are respectively connected with wire rope for driving the pulling vehicle to move back and forth inside the inspection passage;

a winch provided with a single winding drum;

wire tension mechanisms arranged at front and rear ends of said inspection passage, respectively;

wherein said wire rope connected to said front and rear ends of the pulling vehicle (1) is wound around said wire tension mechanisms respectively, and is turned around by a swerving pulley which is positioned at the same horizontal plane as that of said wire tension mechanisms, then the wire rope passes through a vertical pulley block, and finally connected to a single winding drum of said winch and wound around said single winding drum, respectively.

2. The pulling device for a container inspection system according to claim 1, wherein:

said vertical pulley block is composed of an upper vertical pulley and a lower vertical pulley which are positioned at different levels and spaced apart from each other in a horizontal direction, a lower rim of said lower vertical pulley are arranged at the same horizontal plane as that of said swerving wheel, and said position of the upper vertical pulley corresponds to that of said single winding drum, and said wire rope connected with front and rear ends of said pulling vehicle sequentially passes through said lower vertical pulley from a lower side of the lower vertical pulley, then passes through said upper vertical pulley from an upper side of said upper vertical pulley, finally winds around said single winding drum from a lower side to an upper side of said single winding drum respectively.

3. The pulling device for a container inspection system according to claim 2, wherein:

each of said wire tension mechanisms is an active type tension mechanism which generates a tensile force by use of a spring or similar device.

4. The pulling device for a container inspection system according to claim 1, wherein:

each of said wire tension mechanisms is an active type tension mechanism which generates a tensile force by use of a spring or similar device.

* * * * *